(12) United States Patent
Presti

(10) Patent No.: US 8,413,666 B2
(45) Date of Patent: Apr. 9, 2013

(54) ENZYMATIC HAIR RELAXING AND STRAIGHTENING

(75) Inventor: Richard A. Presti, Airmont, NY (US)

(73) Assignee: Beilis Development, LLC, Fair Lawn, NJ (US)

( * ) Notice: Subject to any disclaimer, the term of this patent is extended or adjusted under 35 U.S.C. 154(b) by 42 days.

(21) Appl. No.: 12/503,358

(22) Filed: Jul. 15, 2009

(65) Prior Publication Data

US 2010/0012142 A1    Jan. 21, 2010

Related U.S. Application Data

(60) Provisional application No. 61/081,085, filed on Jul. 16, 2008.

(51) Int. Cl.
*A45D 7/06* (2006.01)

(52) U.S. Cl.
USPC ........... 132/206; 132/203; 132/204; 132/205; 424/70.2

(58) Field of Classification Search .................. None
See application file for complete search history.

(56) References Cited

U.S. PATENT DOCUMENTS

| | | | | |
|---|---|---|---|---|
| 4,279,996 A | * | 7/1981 | Yoshioka et al. | 435/68.1 |
| 5,294,230 A | * | 3/1994 | Wu et al. | 8/127.51 |
| 6,730,493 B1 | * | 5/2004 | Schwan-Jonczyk et al. | 435/23 |
| 2004/0180016 A1 | * | 9/2004 | Buck | 424/70.2 |

OTHER PUBLICATIONS

Lal et al., In vitro degradation of keratin by two species of Bacillus, J. Gen. Appl. Microbiol., 45, 283-287 (1999).*

* cited by examiner

*Primary Examiner* — Daniel Sullivan
*Assistant Examiner* — Barbara Frazier
(74) *Attorney, Agent, or Firm* — Louis C. Paul

(57) ABSTRACT

A method to gently and permanently relax or straighten hair utilizes a protease enzyme, and preferably the enzyme kerA. The hair is optionally treated with a swelling agent, after which it is treated with the enzyme in an aqueous solution. The hair is then physically manipulated, such as by ironing, to remove unwanted curl, wave, and or kink. The enzyme has the ability to cleave inter-peptide bonds, allowing the hair fiber to be relaxed or straightened with less damage to the fiber than would have occurred using traditional or existing straightening methods.

5 Claims, 3 Drawing Sheets

FIG. 5

|  | Average % Change in Strain-to-break | Standard Deviation | Average % Change in Stress-to-break | Standard Deviation |
|---|---|---|---|---|
| Control Formulation | 8.73 | 11.83 | -9.7 | 19.34 |
| Test Formulation | -3.17 | 19.83 | -3.21 | 11.35 |

ENZYMATIC HAIR RELAXING AND STRAIGHTENING

The present application claims the benefit of U.S. Provisional Application 61/081,085 filed Jul. 16, 2008.

FIELD OF THE INVENTION

The present invention relates to hair relaxing and straightening and, more particularly, to the use of enzymes to gently relax or straighten hair.

BACKGROUND OF THE INVENTION

Many women are unhappy with the appearance of their hair. Many women have hair with some degree of curl or kink, and these women frequently desire to relax or straighten their hair using one of several available methodologies.

There are a number of methods available to straighten or relax wavy, curly, kinky or frizzy hair. Some of these methods have existed in some fashion for many years (lye, no-lye, thioglycolates/perm solutions), while others are relatively new (the so-called Japanese and Brazilian methods).

The above mentioned methods for straightening or relaxing hair can be very effective. However, the most effective of these methods generally use harsh chemicals, including sodium hydroxide, potassium hydroxide, lithium hydroxide, guanidine hydroxide, ammonium thioglycolate or sodium sulfide. These chemicals can literally burn the scalp or the eyes of the consumer and always result in the loss of hair tensile strength and excessively weakened hair that is prone to breakage. Other hair relaxing or straightening methods which have gained popularity as of late are either very expensive and time consuming, or employ the use of potentially deadly formaldehyde. Additionally, these so-called safe and chemical free methods often times are not as effective as other treatments for long term straightening of the hair.

It is therefore an object of this invention to provide a method for permanently relaxing or straightening curly, fizzy or kinky hair.

It is therefore a further object of this invention to provide a mild system capable of relaxing and straightening curly, frizzy or kinky hair without the use of harsh chemicals or oxidizing/reducing agents.

SUMMARY OF THE INVENTION

In accordance with foregoing objects, the present invention provides a method for enzymatically relaxing or straightening wavy, curly, kinky or frizzy hair.

Keratin is a key component of the hair fiber. This fiber is a protein having a high concentration of the amino acids gylcine, glutmamic acid and cysteine. However, during the formation of the keratin fiber the sulfhydryl functions of the cysteine residues oxidize to create disulfide bonds that give hairs their structure. Due to the high degree of disulfide cross linking, hydrogen bonding and hydrophobic interactions, keratin is not degradable by proteolytic enzymes such as trypsin, pepsin or papain. However, it have been discovered that certain enzymes, and particularly a keratinase isolated from *Bacillus licheniformis*, show the ability to digest or biodegrade keratinous materials.

It has been demonstrated that such enzymes have the ability to cleave inter-peptide bonds, allowing the hair fiber to be permanently relaxed. Furthermore, the method of the present invention is able to permanently relax or straighten hair with minimal loss of the hair fiber's tensile strength. In accordance with the invention, the hair fibers are treated with a enzyme-containing solution to degrade the hair keratin. The hair is then physically re-oriented to reduce curl, wave, and/or kink, such as by ironing. The hair retains its new orientation.

BRIEF DESCRIPTION OF THE FIGURES

A fuller understanding of the invention will be achieved upon consideration of the following description of a preferred, but nonetheless illustrative, embodiment of the invention when reviewed in conjunction with the annexed figures, wherein:

FIG. 5 is a chart comparing changes in tensile strength of hair fiber after treatment with a no-lye relaxer and the present invention.

DETAILED DESCRIPTION OF THE INVENTION

Figure 1:
FIG. 1 is a photograph of a lock of naturally curly Caucasian hair prior to treatment in accordance with the invention.

Hair is a complex tissue consisting of several morphological components, with each component consisting of several chemical species. Human hair is composed of approximately 65%-95% protein, with the majority being keratin. The remaining constituents are water, lipids (both structural and free), pigment (pheomelanin or eumelanin) and trace elements.

The hair fiber is a cylindrical, keratinized, often pigmented filament. The hair fiber is composed of three parts. From outermost to innermost, the parts of a hair fiber are; the cuticle, the cortex, and the medulla (only present in large terminal hairs, i.e. hairs greater than about 60 microns in diameter).

The cuticle layer of the hair consists of clear, colorless overlapping imbricated cells, akin to shingles on a roof or scales on a fish. These cells are cemented to one another via the action of lipids, the predominant one being 18-methyl eicosanoic acid, and to a lesser extent ceramides and cholesterol. The main function of the cuticle layer is to protect the underlying softer cortex and medulla and to provide the mechanical strength of the hair fiber. A healthy, intact cuticle layer presents an impenetrable barrier to nearly any foreign insult, including a partial exclusion of water.

The hair fiber cortex by weight and volume constitutes the bulk of human hair. The cortex is responsible for the outward morphology of the fiber as well as providing elasticity. Within each cortical cell are bundles of protein known as fibrils which run parallel to the fiber axis, and between fibrils is a softer material called the matrix. The cortex is also where pigment granules are located.

Within the center of the cortex there is a central hollow core, the medulla. In human hair, the medulla may be as much as one third of the diameter of the hair fiber, and may be continuous, discontinuous, or fragmental. In coarse hairs it is usually continuous or fragmental, whereas in fine hairs it appears discontinuous or absent.

In order to permanently alter the morphology of the hair fiber (i.e. permanently relaxing or straightening it), the chemical structure of the cortex must be altered. Conventional two step oxidizing/reducing systems accomplish this by first exposing the hair fiber to a high pH system to de-fat and raise the cuticle, while concomitantly allowing a reducing agent to cleave inter-fibril disulfide linkages. The hair fibers are then moved relative to their initial positions and treated with an oxidizing agent to re-form the disulfide linkages. Alkaline relaxers (including those marketed as no-lye relaxers) are able to permanently relax or straighten any hair type. These types of products work at a very high pH and completely de-fat the cuticle and randomly hydrolyze many of the proteins in the cortex. Although this can result in a permanent alteration of the morphology of the hair, it will also result in a fiber that is exceedingly damaged and prone to breakage.

In accordance with the present invention, in order to facilitate entry of the keratinase into the cortex of the hair, it may be necessary to lift the outer cuticle of the hair fiber. As mentioned, this cuticle prevents the influx of materials into the interior of the hair shaft, necessitating the use of a basic (pH) swelling solution or vehicle to allow the treatment solution to penetrate into the cortex. Alternatively, the pretreatment base may consist of a hypertonic solution, which serves to remove much of the water from the hair shaft. When this partially dehydrated hair is then treated with the treatment solution, the returning influx of water serves to carry the keratinase into the cortex.

The methodology of the present invention includes treatment by a solution containing an enzyme capable of digesting the keratinous hair material. The enzyme is a protease, preferably a serine, and most preferably the keratinase enzyme kerA isolated from *Bacillus licheniformis* PWD-1, obtained from BioResources International, Inc. of Morrisville N.C. The solution consists of an aqueous vehicle buffered to the optimal functional pH of the enzyme. Not unlike most enzymes, kerA keratinase isolated from *Bacillus licheniformis* shows optimal proteolytic activity at a pH of about 7.5. *Bacillus licheniformis* is a ubiquitous bacterium of environmental importance, as it is a contributor to nutrient cycling. *Bacillus lincheniformis* has been used for several decades in the fermentation industry for the production of proteases, antibiotics, amylases, and other specialty enzymes, including those used in laundry detergents.

It has been demonstrated that human hair treated with a combination of the pre-treatment swelling solution with subsequent application of a kerA treatment solution was able to permanently remove 100% of the curl from tightly curled, virgin Caucasian hair (hair supplied by International Hair Importers, Glendale, N.Y.). The identical treatment was also permanently able to remove approximately 70%-95% of the curl from very tightly kinked, virgin African American hair (hair supplied by International Hair Importers, Glendale, N.Y.). Furthermore, this observed straightening effect was achieved with a marked improvement in hair fiber strength relative to a commercial no-lye relaxer.

The current invention can be used as an adjunct to current hair straightening or relaxing methods. Current methods of hair straightening employ chemical agents such as sodium hydroxide, potassium hydroxide, lithium hydroxide, guanidine hydroxide, ammonium thioglycolate, or sodium sulfide at levels high enough to alter the morphology of hair. However, the necessitity of use at sufficiently high levels to achieve the required activity of these chemicals consequently increases chances of irritation/burning and hair fiber damage. Conversely, using these chemicals concomitantly with a keratinase in accordance with the present invention can allow formulations to be developed where the concentrations of the chemical straighteners are reduced, thereby reducing the overall damage to the fiber as well as reducing the risk of irritation to the consumer. In addition, the current invention does not preclude a hair technician from concurrently straightening or relaxing the hair fiber while oxidatively coloring the hair.

In a most preferred embodiment, the hair to be relaxed or straightened is first treated with a swelling solution. The swelling solution can include, but is not limited to, an agent to gently lift the hair cuticle, including ethanolamine, diethanolamine, triethanolamine, aminomethyl propanol or ammonia. Preferably, the agent is present at a percentage of about 0.1 to 25 percent by weight. The swelling solution can also include agents to soften the fiber including, but not limited to, urea. The swelling solution may further contain penetration enhancers to facilitate entry of the keratinase into the hair including, but not limited to, oleic acid, ethoxydiglycol, laurocapram, or pentylene glycol. A preservative system may also be incorporated into the swelling solution formulation to prevent against microbial contamination. Examples of such preservation agents include, but are not limited to, phenoxyethanol, caprylyl glycol, sorbic acid, postassium sorbate, methylchloroisothiazolinone, methylisothiazolinone, methylparaben, ethylparaben, propylparaben and/or butylparaben.

Further, the swelling solution may also contain a surfactant to structure the system and facilitate rinse-off. Examples of surfactants that can be used in the swelling base include, but are not limited to, sodium lauryl sulfate, sodium laureth sulfate, ammonium lauryl sulfate, ammonium laureth sulfate, cocamidopropyl betaine, lauramidopropyl betaine, glycereth-31, sodium lauroyl sarcosinate, cocamidopropyl hydroxysultaine, oleth-5, and/or oleth-10. The swelling base may also contain elements to protect the integrity of the hair including, but not limited to, hydrolyzed wheat protein, hydrolyzed soy protein, hydrolyzed rice protein, or sodium laneth-40 maleate/styrene sulfonate copolymer.

Alternatively, the swelling solution may consist of a solution to facilitate the entry of the enzyme into the cortex of the hair during treatment with the treatment solution. Such a solution may be in the form of a hypertonic swelling solution consisting of, for example, solutions of sodium chloride, magnesium sulfate, sorbitol and/or sucrose.

The hair to be relaxed or straightened is then treated with a treatment solution in the form of a buffered solution of the keratinase, such as kerA from *Bacillus licheniformis*. The treatment solution is most preferentially a buffered system, buffered to a pH equal to the optimal operating pH of the enzyme, with the keratinase being present at about 0.01 to 10 percent by weight. The buffering agent may be present at a weight percentage of about 0.05 to 2.0, to maintain a pH of the treatment solution at between 7.0 and 8.5.

The buffering system can include, but is not limited to, a phosphate buffering system, a carbonate buffering system, or an acetate buffering system. The treatment solution may also contain viscosity-enhancing agents including, but not limited to, xanthan gum, hydroxyethylcellulose, guar gum, locust bean gum, or carbomer. The treatment solution may also contain a preservative system to prevent against microbial contamination. Examples of preservation agents include, but are not limited to, phenoxyethanol, caprylyl glycol, sorbic acid, postassium sorbate, methylchloroisothiazolinone, methylisothiazolinone, methylparaben, ethylparaben, propylparaben or butylparaben. The treatment solution may also contain an agent to gently lift the hair cuticle, including ethanolamine, diethanolamine, triethanolamine, aminomethyl propanol or ammonia. The treatment solution base can also include agents to soften the fiber including, but not limited to urea.

The hair that has been treated with the swelling solution followed by the treatment base is then rinsed, and the hair is flat ironed until the desired morphology of the fiber is achieved.

In the most preferred embodiment, the hair may be treated with the swelling solution for about 25 minutes at 25° C. The hair is then treated with the treatment solution buffered to a pH of 7.5 and held at a temperature of 45° C. for about 45 minutes. At the elevated temperature the treatment solution partially digests the keratinous material in the hair. The hair is then removed from the treatment solution, stopping the digestion action and flat ironed to physically force the hair into a straight orientation and remove or reduce its curl, wave and/or kink to the desired degree. The hair fibers then remain in the straightened orientation without return to their original orientation. Twenty-four hours post treatment the hair can be washed.

Figure 2:
FIG. 2 is a photograph of a lock of naturally curly Caucasian hair post treatment according to the invention.
Figure 3:
FIG. 3 is a photograph of a lock of virgin African American hair prior to treatment in accordance with the invention.
Figure 4:
FIG. 4 is a photograph of a lock of virgin African American hair post treatment according top the invention.

FIGS. 1 and 2 present illustrations of naturally curly Caucasian hair pre- and post-treatment in accordance with the invention. Hair tresses of 2 g were treated with kerA as per the invention, and washed 24 hours post-treatment. The hair tresses were allowed to air dry. Substantial straightening resulted. FIGS. 3 and 4 likewise illustrate the treatment of African American hair. In this figure, hair tresses of 0.3 g were treated as per invention with kerA, and washed 24 hours post-treatment. The hair tresses were allowed to air dry. Once again, substantial straightening resulted.

FIG. 5 is a chart depicting the change in tensile strength of hair fiber after treatment with a no-lye relaxer (control formulation) and a formulation of the present invention (test formulation). Tensile strength was measured with Instron brand tensile measurement equipment. The present invention demonstrated substantially decreased change in fiber strength in comparison to the conventional relaxer.

What is claimed is:

1. A method for straightening hair, comprising the steps of: treating the hair with a treatment composition containing from about 0.01% to 10% of a serine protease enzyme that is kerA isolated from Bacillus licheniformis PWD-1; and applying a post-treatment force to the hair to physically reduce curl, wave and or kink, wherein:
    i) the treatment composition is buffered to between pH 7.0 and 8.5;
    ii) the treatment composition is applied to the hair which is maintained at a temperature of about 45 degrees C.; and
    iii) the treatment composition partially digests the keratinous material in the hair to be treated.

2. The method of claim 1, further including a step of pre-treating the hair with a composition including a swelling agent.

3. The method of claim 2, wherein the swelling agent is present in the composition at a weight percentage of about 0.1% to 25% of one or more swelling agents and the composition is an aqueous composition.

4. The method of claim 1, wherein the temperature is maintained for about 45 minutes.

5. The method of claim 1 wherein the treatment composition is buffered to a pH of about 7.5.

* * * * *